United States Patent [19]

Bartoszek-Loza

[11] 4,451,343

[45] May 29, 1984

[54] PHOTO-INITIATORS FOR DECARBOXYLATION REACTIONS

[75] Inventor: Rosemary Bartoszek-Loza, Solon, Ohio

[73] Assignee: The Standard Oil Company, Cleveland, Ohio

[21] Appl. No.: 528,764

[22] Filed: Sep. 2, 1983

[51] Int. Cl.$^3$ .............................................. B01J 19/12
[52] U.S. Cl. ................................................ 204/158 R
[58] Field of Search ................................... 204/158 R

[56] References Cited
PUBLICATIONS

Enla et al., Biochemische Zeitschrift, vol. 51 (1913), pp. 97–106.
Muller, Biochemische Zeitschrift, vol. 178, (1926), pp. 77–78.
Kirk-Othmer, Encyclopedia of Chemical Technology, 3rd Ed., (1981), vol. 13, pp. 355–373, J. Wiley & Sons.

Primary Examiner—Howard S. Williams
Attorney, Agent, or Firm—Thomas P. Schur; Joseph G. Curatolo; Larry W. Evans

[57] ABSTRACT

A process is provided for the selective photochemical decarboxylation of alpha-hydroxy carboxylic acids to the corresponding alcohols. The process is enhanced with the use of photo-initiator compounds.

14 Claims, No Drawings

PHOTO-INITIATORS FOR DECARBOXYLATION REACTIONS

BACKGROUND OF THE INVENTION

The present invention relates to a process for the photochemical decarboxylation of alpha-hydroxy carboxylic acids. More specifically, the invention relates to a process for initiating the photochemical decarboxylation of alpha-hydroxy carboxylic acids to form the corresponding alcohols.

Photo-initiated reactions may offer economical processes for the conversion of chemical compounds to other chemicals. Specifically, photochemical reactions may provide a reaction path for the conversion of alpha-hydroxy carboxylic acids to the corresponding alcohol. As an example, lactic acid may be photochemically decarboxylated to form other useful chemicals such as the corresponding alcohol which is ethanol and also methanol, butanol, acetone, acetaldehyde, 2,3-butanediol, acetic acid, propionic acid, alpha-ketoglutaric acid, citric acid, gloxylic acid, fumaric acid and other polyhydroxy and polycarboxylic compounds.

Photochemical reactions are known in which an alpha-hydroxy carboxylic acid does form the corresponding alcohol, but only in negligible yields. Generally, such photochemical processes utilize a catalyst. Catalyzed photochemical reations may provide a process for the production of enhanced yields of the corresponding alcohol from the decarboxylation of an alpha-hydroxy carboxylic acid.

Euler and Ryd reported in *The Decomposition of Lactic Acid and Tannic Acid in Ultraviolet Light,* Biochemische Zeitschrift, Vol. 51, pp. 97–103, 1913, that lactic acid undergoes cleavage at 70° C. in the presence of ultraviolet light to form formic acid and acetaldehyde and that these products were in turn rapidly converted to ethanol and carbon dioxide. Euler and Ryde also reported using mineral acids, such as iron and magnese salts, to accellerate the cleavage of lactic acid. Mueller disclosed the use of uranyl and iron salts to catalyze the conversion of lactic acid to ethanol. Mueller, R., *The Quantum Sensitivity of the Decomposition of Lactic Acid, Uranyl Sulfate,* Biochemische Zeitschrift, Vol. 178, pp. 77–78, 1926. The amount of ethanol produced from lactic acid in the above references is very low.

Commonly a photosensitizing agent is used in conjunction with a catalyst to enhance the performance of the catalyst. The combination of photosensitizer and catalyst may produce high yields of a desired product and/or faster reaction rates of conversion when compared to the singular use of the photosensitizer or catalyst. However, such processes are generally expensive to operate.

It would be a significant contribution to the field of photochemical alpha-hydroxy carboxylic acid degradation to provide a process that produces a high yield of the corresponding alcohol and/or fast reaction rates to form the corresponding alcohol. Therefore, it is an object of the present invention to provide a process for the photochemical decarboxylation of an alpha-hydroxy carboxylic acid to the corresponding alcohol in improved yields and/or reaction rates by irradiating the alpha-hydroxy carboxylic acid in the presence of a photochemical initiator.

The above object and other objects of the present invention, together with the advantages thereof, will become apparent from the following specification and appended claims.

SUMMARY OF THE INVENTION

The present invention relates to a process for the photochemical decarboxylation of an alpha-hydroxy carboxylic acid to form high yields of the corresponding alcohol comprising irradiating a mixture of (a) a solution containing the alpha-hydroxy carboxylic acid and (b) a free radical initiator selected from the group consisting of peroxide and azo compounds.

DETAILED DESCRIPTION OF THE INVENTION

In accordance with this invention, there is provided a free radical initiator compound and a process whereby the free radical initiator compound enhances the yield of alcohols formed by the decarboxylation of alpha-hydroxy carboxylic acids.

Alpha-hydroxy carboxylic acids may be represented by the formula

R—CHOH—COOH, wherein R may be hydrogen or an alkyl, alkenyl, aryl, alkaryl, cycloalkyl or cycloalkenyl radical having from 1 to about 20 carbon atoms, and preferably having from 1 to about 12 carbon atoms.

Typical alpha-hydroxy carboxylic acids include mandelic acid, alpha-hydroxy isobutyric acid, alpha-ethyl-alpha-hydroxybutyric acid, alpha-hydroxy-alpha-methylbutyric acid, alpha-isopropyl-mandelic acid, lactic acid, benzylic acid and phenyllactic acid.

The reaction by which alpha-hydroxy carboxylic acids are converted to alcohols may be represented by the formula (I) below.

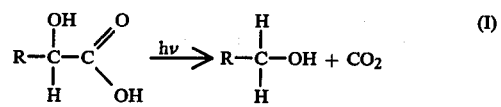

(I)

When the alpha-hydroxy carboxylic acid is lactic acid and is photochemically converted in accordance with this invention, the corresponding alcohol that is formed in high yields is ethanol.

Other hydrocarbon reaction products from the photochemical decarboxylation of alpha-hydroxy carboxylic acids include other alcohols and acids, diols, aldehydes and lactones.

In accordance with the process of this invention an alpha-hydroxy carboxylic acid in solution is contacted with a free radical photo-initiator compound and irradiated to cause the formation of free radicals by the photo-initiator compound which enhance the photo-induced decarboxylation of the alpha-hydroxy carboxylic acid to its corresponding alcohol.

The alpha-hydroxy carboxylic acid is disposed in a solution which may be an aqueous solution or a suitable organic solution in which the alpha-hydroxy carboxylic acid is soluble and which does not interfer with the performance of the free radical initiator nor block high energy spectral light, such as acetonitrile. Preferably, the solution is an aqueous solution. For optimum alcohol yield and reaction rates it is preferred that the alpha-hydroxy carboxylic acid be present in solution at an initial molar concentration of from about 0.5 M to about 1.0 M, and most preferred to have an initial alpha-hydroxy carboxylic acid concentration of from about 0.80 M to about 0.90 M.

In accordance with this invention the free radical initiator is placed in contact with the alpha-hydroxy carboxylic acid. The photo-initiator may be in the form of a powder wherein it is preferably mixed uniformly into the alpha-hydroxy carboxylic acid solution or may be on a high surface area fixed bed disposed in the alpha-hydroxy carboxylic acid solution. The free radical photo-initiator may be present in solution at any concentration. Preferably the photo-initiator is present in solution at a minute concentration of only from about 0.0005 M to about 0.02 M. Optimally, the free radical photo-initiator is present in the alpha-hydroxy carboxylic acid solution at a concentration of from about 0.001 M to about 0.0025 M. The free radical initiator may also be deposited in a reaction chamber in a form of packed pellets. The process of this invention may be adaptable for both batch and continuous operations.

The photo-initiator compound enhances the selective photo-induced decarboxylation of alpha-hydroxy carboxylic acids to respective alcohols. The photo-initiator compound absorbs actinic radiation, forming reactive free radical intermediates that react further with the alpha-hydroxy carboxylic acids in solution. A general discussion of chemical reaction initiators is available in Kirk-Othmer, Encyclopedia of Chemical Technology, Vol. 13, pp. 355-373, "Initiators", John Wiley and Sons, 1978.

Peroxides and azo compounds are principally utilized as thermal free radical initiators, but are also known to be photochemically unstable and have been used as free radical sources at temperatures below their normal thermal decomposition temperatures. In accordance with this invention, it has been found that peroxide and azo compounds selectively enhance the photochemical decarboxylation of alpha-hydroxy carboxylic acids to the corresponding alcohols.

Typical peroxides which may be used to initiate the photochemical decarboxylation of alpha-hydroxy carboxylic acids include diacyl peroxides, peroxyesters, diperoxyketals, dialkyl peroxides and peroxydicarbonates. Preferred peroxide compounds include diacyl peroxides, acetyl alkylsulfonyl peroxides, dialkyl peroxydicarbonates, tert-alkyl peroxyesters, OO-tert-alkyl O-alkyl monoperoxycarbonates, di(tert-alkylperoxy)ketals, di-tert-alkyl peroxides, tert-alkyl hydroperoxides and ketone peroxides.

Most preferred peroxide compounds for utilization as photo-initiators as disclosed herein are the diacyl peroxides such as dibenzoyl peroxide, di(2,4-dichlorobenzoyl) peroxide, diacetyl peroxide, dilauroyl peroxide and diisobutyryl peroxide.

Typical azo compounds which function as photo-initiators for the decarboxylation of alpha-hydroxy carboxylic acids to the respective alcohols include the symmetrical azonitriles and the unsymmetrical tert-butylazonitriles. Preferably, the azo photo-initiator is an unsymmetrical tert-butylazonitrile such as
2,2'-azobis(2,4-dimethyl)pentanenitrile,
2-(tert-butylazo)-4-methoxy-2,4-dimethyl-pentanenitrile,
2,2-azobis(isobutyronitrile),
2-(tert-butylazo)isobutyronitrile,
2-(tert-butylazo)-2-methylbutanenitrile,
1,1-azobis-cyclohexanecarbonitrile,
1-(tert-amylazo)cyclohexanecarbonitrile and
1-(tert-butylazo)cyclohexanecarbonitrile.

A catalyst which is known to enhance the decarboxylation of alpha-hydroxy carboxylic acids to the corresponding alcohols may be utilized with a free radical photo-initiator of this invention to further enhance the yield of the corresponding alcohol but is not necessary to the invention. Uranyl salts are examples of known catalysts for the photochemical decarboxylation of alpha-hydroxy carboxylic acids.

In accordance with the process of this invention, the alpha-hydroxy carboxylic acid solution in contact with a free radical photo-initiator (and optionally in contact with a catalyst) is irradiated to induce a photochemical reaction. The source of irradiation may be solar or an artifical light. The light source preferably includes wavelengths in the range of from about 2,200 Å to about 14,000 Å. Optimally, the light source irradiating the mixture of alpha-hydroxy carboxylic acid solution and free radical photo-initiator includes light having a substantial irradiation spectrum in the range from about 2,200 Å to about 4,000 Å.

The process may proceed under a wide range of temperatures, pressures and atmospheres and still provide the photo-induced decarboxylation of alpha-hydroxy carboxylic acids to the corresponding alcohols. Optimum reaction conditions will be dependent on the particular reactants used. Preferably, the photo-induced decarboxylation of alpha-hydroxy carboxylic acids in the presence of a free radical initiator occurs at temperatures of from about 0° C. to about 100° C., pressures of from about 1 atmosphere to about 10 atmospheres and under an oxidative or inert atmospheres. More preferred, the photochemical reaction occurs at from about 0° C. to about 50° C., from about 1 to about 3 atmospheres and under an atmosphere of nitrogen, helium, argon, oxygen or air. Optimally, alpha-hydroxy carboxylic acids are photochemically converted to the corresponding alcohols in the presence of a free radical initiator at temperatures of from about 20° C. to about 30° C., at about atmospheric pressure and under an atmosphere of nitrogen, argon or air.

The photo-induced decarboxylation of alpha-hydroxy carboxylic acids in accordance with the present invention yields primarily the corresponding alcohols and secondarily other alcohols, acids, diols, aldehydes and lactones. The free radical initiator and the hydrocarbon products may be separated from the reaction mixture and from each other by known separation techniques such as filtration, distillation and/or extraction.

The alcohols produced by this process are useful as fuels and as intermediates for the production of other chemicals.

EXAMPLES

The above-described invention may be more clearly understood by the following examples which are not intended to be limitative of the invention in any way.

EXAMPLES 1-6

The following examples measure ethanol yield from the photochemical decarboxylation of lactic acid with and without a free radical initiator being present and with and without an optional catalyst being present in the reaction solution. It is understood that any alpha-hydroxy carboxylic acid would react in a manner similar to that exhibited by lactic acid hereunder.

The examples were performed in a 500 ml photochemical reaction vessel containing a stirring bar therein and a water-cooled, double-walled quartz immersion well which maintained the reaction at a temperature of between about 23° C. and about 28° C. and contained a light source therein. A water-cooled Friedrich condenser was disposed over the reaction vessel to minimize loss of hydrocarbon products, such as ethanol, by evaporation. The reaction vessel was closed to the atmosphere above the condenser.

A lactic acid solution was prepared by dissolving 31.5 grams 88 percent lactic acid (0.88 M) into 350 ml of distilled water. A known amount of free radical initiator and/or catalyst in the form of powders was then admixed into the lactic acid solution to form an activated solution. In the control example, Example 1, no free radical initiator or catalyst was added.

The activated solution was then disposed in the photochemical reaction vessel and stirred while irradiated with a light source having the following spectral energy distribution (recorded in watts):

| Far UV | 2,200–2,800Å | 29.2 watts |
| Middle UV | 2,800–3,200Å | 32.8 watts |
| Near UV | 3,200–4,000Å | 32.9 watts |
| Visible | 4,000–10,000Å | 87.2 watts |
| Infrared | 10,000–14,000Å | 20.6 watts |

Each solution was irradiated for a period of time until, based on sampling, the formation of additional photoproducts ceased. The reacted solution was analyzed by gas chromatography and gas chromatography/mass spectroscopy to identify the photoproducts. The final reaction mixture was characterized and the percent ethanol yields, based on the number of moles of lactic acid reacted, were determined and are reported in Table I.

These examples demonstrate the effectiveness of the free radical photo-initiator for enhancing alcohol yield produced by irradiating an alpha-hydroxy carboxylic acid solution, with or without an optional catalyst being present. No free radical photo-initiator was used in Examples 1 and 2. The free radical photo-initiator of Examples 3 and 4 was azobisisobutyronitrile, while benzoyl peroxide was used in Examples 5 and 6. As can be seen in Table 1, Examples 1, 3 and 5, the use of a free radical photo-initiator significantly increases ethanol yield from an irradiated lactic acid solution as compared to a control lactic acid solution which contained no free radical initiator. The ethanol yield of Example 1, the control example, was about 15 percent. The ethanol yield of Example 3, wherein azobisisobutyronitrile was added as a free radical photo-initiator was 20 percent, about a 30 percent increase over Example 1. When benzoyl peroxide was added as the photo-initiator, as in Example 5, the ethanol yield was about 22 percent, about a 47 percent increase over Example 1.

As is determined from examining Examples 2, 4 and 6, the presence of a free radical photo-initiator also increased ethanol yield of lactic acid solution having a catalyst therein. In Example 2, a uranyl acetate catalyst was added to a lactic acid solution that yielded about 37 percent ethanol. When azobisisobutyronitrile, a photo-initiator in accordance with this invention, was added to a lactic acid solution, as in Example 4, the resultant ethanol yield was about 44 percent, about a 19 percent increase as compared to Example 2. Example 6 utilized a benzoyl peroxide photo-initiator in a lactic acid solution that contained uranyl acetate catalyst to produce an ethanol yield of about 48 percent, about a 30 percent increase over Example 2 which comprised a lactic acid solution containing only uranyl acetate catalyst and over 220 percent more than the control solution of lactic acid in Example 1.

These examples clearly demonstrate the enhancing effect produced by using free radical photo-initiators for the photochemical decarboxylation of alpha-hydroxy carboxylic acids to produce the corresponding alcohols.

TABLE 1

ALCOHOL YIELD OF PHOTO-INDUCED DECARBOXYLATION REACTIONS

| EXAMPLE | ACTIVATED MIXTURE | | IRRADIATION TIME (HR) | ETHANOL YIELD (PERCENT) |
|---|---|---|---|---|
| 1. | 0.88M | Lactic Acid Solution | 24 | 15 |
| 2. | 0.88M | Lactic Acid Solution | 28 | 37 |
|  | 0.0047M | Uranyl Acetate | | |
| 3. | 0.88M | Lactic Acid Solution | 30 | 20 |
|  | 0.0016M | Azobisisobutyronitrile | | |
| 4. | 0.88M | Lactic Acid Solution | 26 | 44 |
|  | 0.0047M | Uranyl Acetate | | |
|  | 0.0016M | Azobisisobutyronitrile | | |
| 5. | 0.88M | Lactic Acid Solution | 30 | 22 |
|  | 0.002M | Benzoyl Peroxide | | |
| 6. | 0.88M | Lactic Acid Solution | 26 | 48 |
|  | 0.0047M | Uranyl Acetate | | |
|  | 0.002M | Benzoyl Peroxide | | |

EXAMPLES 7–16

The following examples demonstrate the effect of varying the concentration of the photo-initiating compound on the resultant ethanol yield from the photochemical decarboxylation of lactic acid. These examples were performed in the same manner as described in Examples 1–6 with the further specification that each example was irradiated with the above-described light source for 16.5 hours.

In Examples 7–11 the free radical photo-initiator compound was azobisisobutyronitrile. In Examples 12–16 the photo-initiator was benzoyl peroxide. As can be seen from Table 2, minute amounts of photo-initiator compound significantly enhance ethanol yield. In Examples 7–11 the amount of azobisisobutyronitrile ranged from about 0.00171 M to about 0.0205 M and ethanol yield ranged from about 20 percent to about 13 percent, respectively. In Examples 12–16 the amount of benzoyl peroxide in the lactic acid solution ranged from about 0.00091 M to about 0.00902 M and the ethanol yield ranged from about 22 percent to about 9 percent, respectively.

The ethanol yield of Examples 7–16 may be compared to the ethanol yield obtained when a control lactic acid solution was irradiated, as in Example 1 wherein the ethanol yield was only 15 percent after twenty-four hours of irradiation. Thus, these examples show that minute amounts of free radical photo-initiator compounds produce an enhanced yield of the corresponding alcohol when present during the photochemical decarboxylation of an alpha-hydroxy carboxylic acid.

TABLE 2

ALCOHOL YIELD AS A FUNCTION OF FREE RADICAL PHOTO-INITIATOR CONCENTRATION

| EXAMPLE | FREE RADICAL PHOTO-INITIATOR, CONCENTRATION | | ETHANOL YIELD (PERCENT) |
|---|---|---|---|
| 7  | Azobisisobutyronitrile, | 0.00171M | 20 |
| 8  |                         | 0.00304M | 16 |
| 9  |                         | 0.00548M | 18 |
| 10 |                         | 0.01350M | 14 |
| 11 |                         | 0.02050M | 13 |
| 12 | Benzoyl Peroxide,       | 0.00091M | 19 |
| 13 |                         | 0.00165M | 22 |
| 14 |                         | 0.00421M | 15 |
| 15 |                         | 0.00744M | 16 |
| 16 |                         | 0.00902M | 9  |

The selection of free radical initiator, alpha-hydroxy carboxylic acids, products derived from the photo-induced decarboxylation thereof and reactant conditions can be determined from the preceeding specification disclosure provided without departing from the spirit of the invention herein disclosed and described; the scope of the invention including modifications and variations that fall within the scope of the appended claims.

We claim:

1. A process for the photochemical decarboxylation of an alpha-hydroxy carboxylic acid to form high yields of the corresponding alcohol comprising irradiating a mixture of (a) a solution containing the alpha-hydroxy carboxylic acid and (b) a free radical initiator selected from the group consisting of peroxide and azo compounds.

2. The process in accordance with claim 1 wherein said alpha-hydroxy carboxylic acid is selected from the group consisting of mandelic acid, alpha-hydroxy isobutyric acid, alpha-ethyl-alpha-hydroxy butyric acid, alpha-hydroxy-alpha-methyl butyric acid, alpha-isopropyl-mandelic acid, lactic acid, benzylic acid, phenyllactic acid, and mixtures thereof.

3. The process in accordance with claim 1 wherein said alpha-hydroxy carboxylic acid is lactic acid.

4. The process in accordance with claim 1 wherein said free radical photo-initiator compound is selected from the group consisting essentially of diacyl peroxides and unsymmetrical tert-butylazonitriles.

5. The process in accordance with claim 1 wherein said free radical initiator compound is selected from the group consisting of azobisisobutyronitrile and benzoyl peroxide.

6. The process in accordance with claim 1 wherein said solution is an aqueous solution.

7. The process in accordance with claim 1 wherein said alpha-hydroxy carboxylic acid is initially present in solution at a molar concentration of from about 0.5 M to about 1.0 M.

8. The process in accordance with claim 1 wherein said alpha-hydroxy carboxylic acid is initially present in solution at a molar concentration of about 0.80 M to about 0.90 M.

9. The process in accordance with claim 1 wherein said free radical initiator compound is present in solution at a concentration of from about 0.0005 M to about 0.02 M.

10. The process in accordance with claim 1 wherein said free radical initiator compound is present in solution at a concentration of from about 0.001 M to about 0.0025 M.

11. The process in accordance with claim 1 wherein there is included a photochemical catalyst material.

12. The process in accordance with claim 11 wherein said included photochemical catalyst material is uranyl acetate.

13. The process in accordance with claim 1 wherein said mixture is irradiated with light having an energy spectral distribution including wavelengths of from about 2,200 Å to about 14,000 Å.

14. The process in accordance with claim 1 wherein said mixture is irradiated with light having an energy spectral distribution including wavelengths of from about 2,200 Å to about 4,000 Å.

* * * * *